(12) United States Patent
Ye

(10) Patent No.: US 9,427,268 B2
(45) Date of Patent: Aug. 30, 2016

(54) POROUS TANTALUM ROD

(75) Inventor: Lei Ye, Chongqing (CN)

(73) Assignee: CHONGQING RUNZE PHARMACEUTICAL CO., LTD., Chongquing (CN)

( * ) Notice: Subject to any disclaimer, the term of this patent is extended or adjusted under 35 U.S.C. 154(b) by 76 days.

(21) Appl. No.: 14/111,257

(22) PCT Filed: Apr. 19, 2012

(86) PCT No.: PCT/CN2012/074345
§ 371 (c)(1),
(2), (4) Date: Oct. 11, 2013

(87) PCT Pub. No.: WO2012/142952
PCT Pub. Date: Oct. 26, 2012

(65) Prior Publication Data
US 2014/0031824 A1    Jan. 30, 2014

(30) Foreign Application Priority Data
Apr. 20, 2011 (CN) .......................... 2011 1 0099357

(51) Int. Cl.
*A61B 17/74* (2006.01)
*A61B 17/86* (2006.01)
*A61B 17/88* (2006.01)

(52) U.S. Cl.
CPC ............. *A61B 17/74* (2013.01); *A61B 17/866* (2013.01); *A61B 17/8875* (2013.01)

(58) Field of Classification Search
CPC .................................................. A61L 31/146
See application file for complete search history.

(56) References Cited

U.S. PATENT DOCUMENTS

| 5,360,448 | A | * | 11/1994 | Thramann | 606/60 |
| 5,364,400 | A | * | 11/1994 | Rego et al. | 606/304 |
| 5,743,912 | A | * | 4/1998 | Lahille | A61B 17/746 606/290 |
| 7,682,704 | B2 | * | 3/2010 | Dwivedi | 428/547 |
| 2003/0153981 | A1 | * | 8/2003 | Wang et al. | 623/22.21 |
| 2004/0225292 | A1 | * | 11/2004 | Sasso | A61B 17/8615 606/916 |
| 2005/0048193 | A1 | * | 3/2005 | Li et al. | 427/2.24 |
| 2006/0003179 | A1 | * | 1/2006 | Wang et al. | 428/613 |
| 2006/0142769 | A1 | * | 6/2006 | Collette | 606/73 |
| 2007/0073385 | A1 | * | 3/2007 | Schaeffer et al. | 623/1.16 |
| 2008/0215098 | A1 | * | 9/2008 | Imwinkelried et al. | 606/301 |
| 2012/0271362 | A1 | * | 10/2012 | Martineau et al. | 606/304 |
| 2013/0011691 | A1 | * | 1/2013 | Ruan et al. | 428/566 |
| 2014/0039565 | A1 | * | 2/2014 | Martineau et al. | 606/304 |
| 2014/0227428 | A1 | * | 8/2014 | Ye | 427/2.24 |

FOREIGN PATENT DOCUMENTS

WO     WO 2011/120280     * 10/2011 ................ B22F 3/11

* cited by examiner

*Primary Examiner* — Jan Christopher Merene

(57) ABSTRACT

A porous tantalum rod is provided, which is a medical implantation used for treating collapsed articular surface of the femoral head or necrosis of the femoral head in phase I or phase II. The implantation includes a fastening structure formed on one end of the porous tantalum rod used for connecting with the osseous tissues and a through hole formed on the center of the porous tantalum rod. The porous tantalum rod is made of the porous tantalum material, which is produced by foam impregnation and had a foam structure with three-dimensional interconnecting pores, wherein the foam structure has a foam skeleton, tantalum particles located on the foam skeleton, and multiple sintering neck structures formed between the tantalum particles.

3 Claims, 5 Drawing Sheets

POROUS TANTALUM ROD

FIELD OF INVENTION

The present invention relates to a medical implantation, especially relates to a porous tantalum rod used for treating collapsed articular surface of the femoral head or necrosis of the femoral head in phase I or phase II.

DESCRIPTION OF THE RELATED ART

Collapsed articular surface of the femoral head and necrosis of the femoral head are common clinical diseases. At present, the drilling method of decompression is usually used for treating collapsed articular surface of the femoral head or necrosis of the femoral head. In the surgery, the sequestrum is needed to remove first before filling the medical implantation for supporting collapse or necrosis of femoral head.

A porous metal material used for medical implantation is important for specific application of treating traumatic osseous tissues, necrotic femoral tissues or the like. Such metal materials are normally porous stainless steel, porous titanium, and so on. As a porous implant material for the treatment of traumatic osseous tissues and necrotic femoral tissues, the porosity thereof should reach to 30-85%, and the pores should be all interconnected and well-distributed or partially interconnected depending on requirement. Thus, the porous implant material can make the growth phase of the osseous tissue uniform and have lower weight to fit the use of medical implantation.

Due to good biocompatibility and mechanical properties of the insoluble tantalum, the porous form thereof is potential in place of the traditional metal biomaterials mentioned above in order to be used as a medical implant material for the application of treating necrotic femoral tissues. Also, due to the harmlessness, non-toxicity, few of side effects, the rapid development of the medicine, and the further knowledge of tantalum as an implant material, the requirement of porous tantalum for medical implantation is getting more urgent than before, and the criterion of the quality of porous tantalum is getting much higher. As a porous tantalum for medical implantation, having a lot of well-distributed interconnecting pores and mechanical properties adaptable to human body are of great importance for being a connecting component to keep the newborn tissues growing well at the positions of traumatic osseous tissues or ossature defects.

Regarding porous tantalum, U.S. Pat. No. 5,282,861 discloses "Open cell tantalum structures for cancellous bone implants and cell and tissue receptors". The porous tantalum is manufactured by commercial tantalum and a supporter such as a carbon skeleton obtained from heat degradation of polyurethane precursors. The carbon skeleton has multiple dodecahedrons with mesh structures inside and wholly distributed pores, and the porosity thereof reaches to 98%. Next, the commercial tantalum is bound to the carbon skeleton to form porous metal microstructure through chemical vapor deposition (CVD) (also called "chemical deposition"). The porous tantalum material obtained by such processes has a tantalum layer having 40-60 μm of thickness, and has about 99 wt % of tantalum and about 1 wt % based on the weight of whole porous tantalum materials. The patent further discloses that the porous tantalum has 50-70 MPa of compressive strength, 2.5-3.5 GPa of elastic modulus, 63 MPa of tensile strength and 15% of the amount of plastic deformation. However, the ductility of the porous tantalum described above is obviously insufficient causing subsequent processing of the porous tantalum, such as cutting the formed material. Similarly, the porous tantalum prepared by such methods mentioned above like foam impregnation has the same problems. Due to the limitation of the manufacturing methods, the obtained products usually are not pure enough and have remaining residues of the carbon skeleton such that the biosafety is much decreased."

Currently, the medical implantation made of porous tantalum material used for filling collapsed articular surface of the femoral head or necrosis of the femoral head is a rod-like body with screw thread formed on one end of the rod-like body. People in the industry is accustomed to call it as a porous tantalum rod used for implanting into the femoral head in clinical treatment and relied on the natural growth of the femoral head to confine and fixed the porous tantalum rod.

The porous tantalum rod with this type of structure is difficult to position precisely in surgery. In the surgery, the screwed structure of the porous tantalum rod is held by special surgical tool and screwed into the femoral head, and inducing one end of screw fixed in the cortical bone of the femoral head decreased. Thus results the porous tantalum rod fixed instability, easy to dislocation, and can't depressurize continually. Overall, the medical implantation with this type of structure has lower success rate in surgery.

SUMMARY OF THE INVENTION

The objective of the present invention is to provide a porous tantalum rod used for medical implantation with convenience of positioning precisely and good mechanical properties.

To achieve the objective, a porous tantalum rod used for medical implantation in accordance with the present invention is including: a fastening structure formed on one end of the porous tantalum rod; a through hole formed on the center of the porous tantalum rod; and the porous tantalum material used on the porous tantalum rod produced by foam impregnation and having a foam structure with three-dimensional interconnecting pores, wherein the foam structure has a foam skeleton, tantalum particles located on the foam skeleton, and multiple sintering neck structures formed between the tantalum particles.

The porous tantalum rod having the sintered neck structure formed between the tantalum particles greatly improves the mechanical properties of such implantation like ductility, anti-bending strength, and easy to drill. The through hole in the center of the porous tantalum rod provides the convenience of precisely positioning in the surgery and convenience to remove and inject correlate, and achieves effect of decompression continually.

Preferably, the fastening structure of the porous tantalum rod is a screwed structure, and had a slotted formed on the end-face of the screwed structure provided surgical tool to use in conjunction with the slotted.

Preferably, the other end of the porous tantalum rod opposite to the fastening structure is ball head shaped.

The shape of the through hole in the center of the porous tantalum rod is circular-shaped, square-shaped or other shapes in cross section.

The porous tantalum rod is made of porous tantalum material made by foam impregnation. Specifically, the method for preparing the porous tantalum material comprising steps of:

(a) providing an organic binder, dispersant and tantalum powder;

(b) mixing the organic binder and the dispersant to form a solution and then mixing the solution and the tantalum powder to form tantalum slurry;

(c) providing an organic foam body, wherein the organic foam body has multiple pores;

(d) casting the tantalum slurry into the organic foam body and impregnating the casted organic foam body with the tantalum slurry until the pores of the organic foam body are filled with the tantalum slurry;

(e) drying the impregnated organic foam body with the tantalum slurry to remove the dispersant;

(f) degreasing the dried organic foam body to separate the dried tantalum slurry from the organic binder and the organic foam body in a protective environment of inert gas;

(g) vacuum sintering the dried tantalum slurry to obtain a porous sintered body, wherein the porous sintered body has a foam skeleton, sintered tantalum particles located on the foam skeleton, and multiple sintering neck structures formed between the tantalum particles; and (h) vacuum annealing and treating the porous sintered body with normal post-treatments to obtain the porous tantalum.

The porous tantalum material made of the method maintains the mechanical properties of the porous tantalum with such sintered neck structure, as well as the improved ductility thereof. Also, the porous tantalum material prepared by such method can be conveniently and effectively used for the application of surgery implantation of medical metal material. The porous tantalum rod made of the method is specially suitable to be a medical implantation used for treating collapsed articular surface of the femoral head or necrosis of the femoral head in phase I or phase II. Furthermore, the method is easy and easy to control, and the processes of the method are harmless, non-polluting, non-toxic, non- dust, no side effects on the human body.

More specifically, the porous tantalum material is produced by sintering the tantalum powder having an average diameter of less than 50 μm and oxygen content in an amount of less than 0.1%, wherein it has 30-85% of porosity and 150-600 μm of pore diameter, and the sintering neck structures are formed between at least 50%-95% of the tantalum particles.

In the method for preparing the porous tantalum material, the organic foam body in the foam impregnation is a polyurethane foam body having 0.48-0.89 mm of pore diameter, 0.015-0.065 g/cm$^3$ of density and larger than 40° of hardness.

In summary, the porous tantalum rod used for medical implantation in accordance with the present invention is including a through hole in the center of the porous tantalum rod. Therefore, the implantation can be passed through the through hole and screwed along the positioning pin (guide pin). After the implantation screwed, the guide pin can be removed easily from the through hole.

Mashed osseous tissues can be injected into the femoral head through a feeder from the through hole, thus causes the cavity of the femoral head without lesion osseous tissues filled more denser and more conducive to fix the implantation and grow of osseous tissues.

The medical implantation made of the porous tantalum material of the present invention is available to long-term preserved in human body, has good support intensity and heals and fixes better with surrounding osseous tissues. More importantly, the through hole formed on the center of the porous tantalum rod is conducive to depressurize continually in intraoperative and postoperative. Overall, the porous tantalum rod of the present invention provides higher success rate in the implant surgery.

DETAILED DESCRIPTION OF THE INVENTION

EXAMPLE 1

Figure 1:
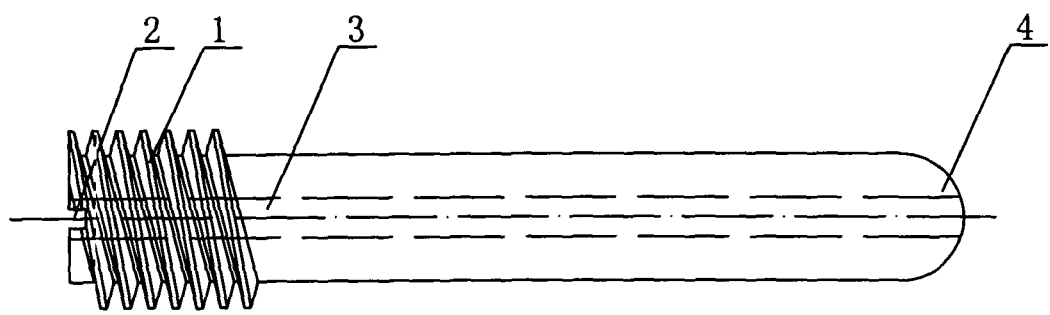
FIG. 1 is a schematic view of an embodiment of a porous tantalum rod in accordance with the present invention.
Figure 2:
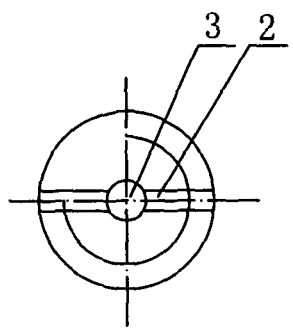
FIG. 2 is a left view of a porous tantalum rod in FIG. 1.
Figure 3:
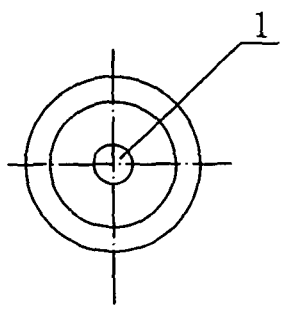
FIG. 3 is a right view of a porous tantalum rod in FIG. 1.

Referring to FIGS. 1 to 3, a porous tantalum rod in accordance with the present invention comprises: a fastening structure 1 with screw thread formed on one end of the porous tantalum rod used for connecting with osseous tissues; a ball head shaped structure 4 formed on the other end of the porous tantalum rod; as shown in FIGS. 2, a slotted 2 formed on the end-face of the fastening structure 1 providing the surgical tools easy to install and use; and a through hole 3 formed on the center of the porous tantalum rod as shown in FIG. 3, wherein the shape of the through hole 3 in cross section is circular-shaped in this example, but also available to square-shaped or other shapes. The through hole is provided the convenience of positioning and convenience to remove and inject correlate. The porous tantalum material of the porous tantalum rod has a foam structure with three-dimensional interconnecting pores, which is produced by foam impregnation. The foam structure has a foam skeleton, and tantalum particles accumulated on the foam skeleton, and multiple sintering neck structures formed between the tantalum particles.

Figure 4:
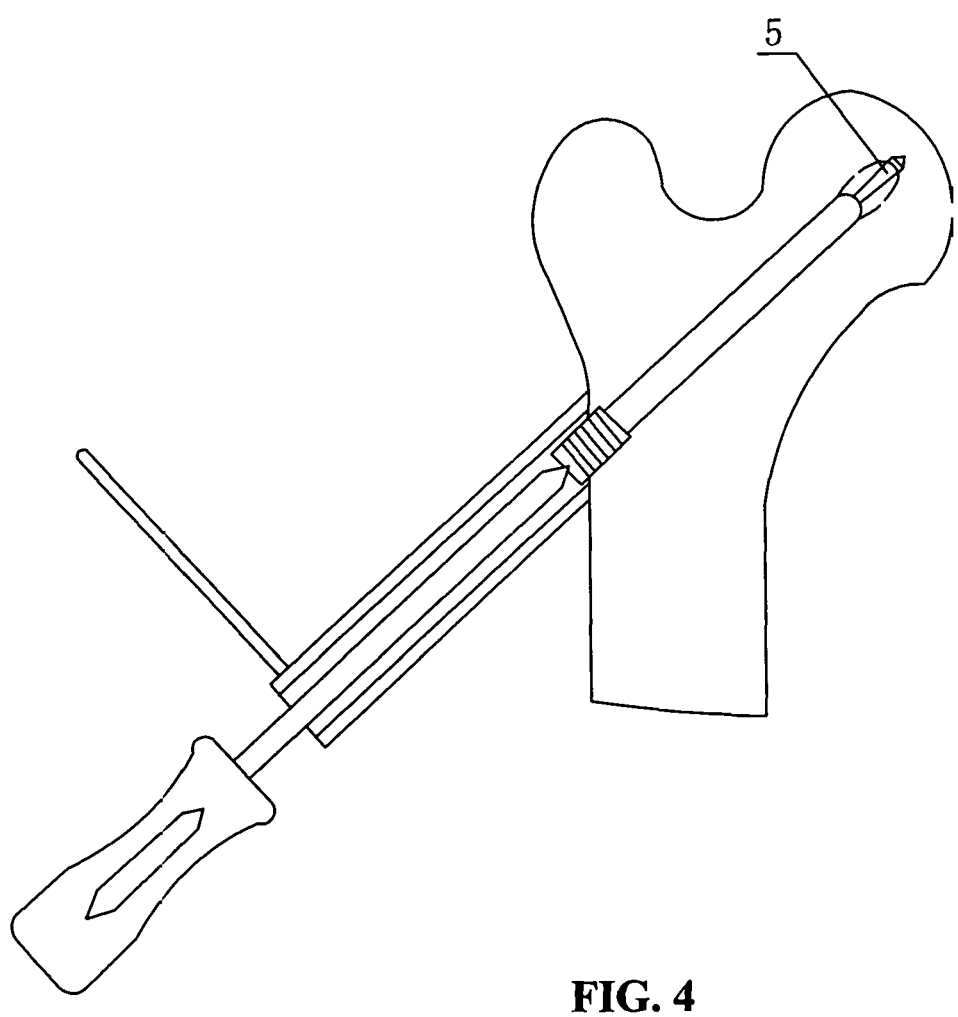
FIG. 4 is a schematic view of a porous tantalum rod localized using guide pin in accordance with the present invention.

Referring to FIG. 4, due to the through hole is in the center of the porous tantalum rod, the implantation is available to be screwed along the guide pin (positioning pin). Screwdriver is matched to the slotted 2 formed on the end-face of the fastening structure and be rotated to screw the implantation when half of implantation.

Preferably, the implantation is a screwed fastening structure, thus the installation of the implantation can be positioned in position precisely.

Figure 5:
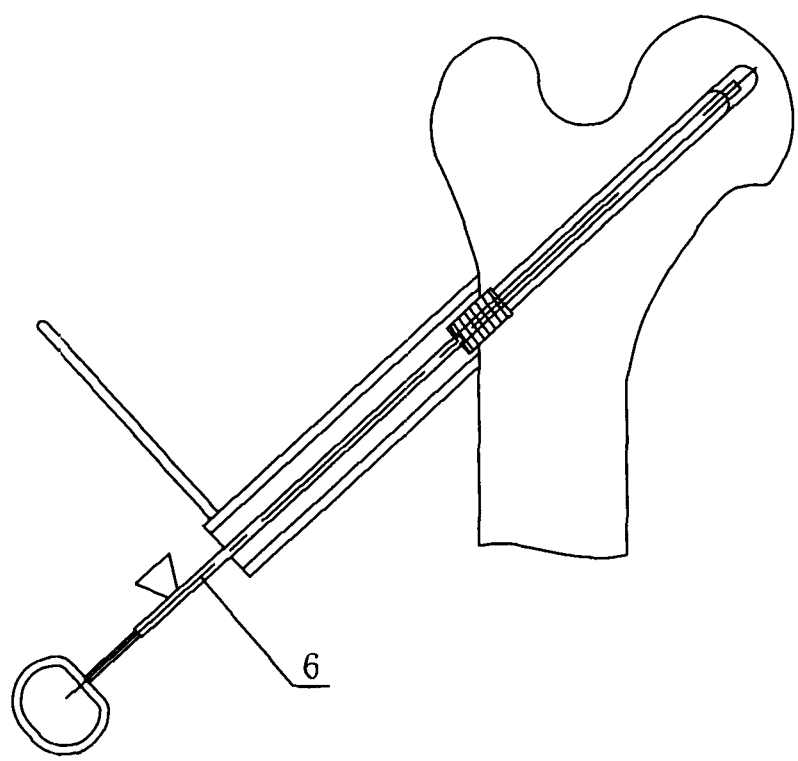
FIG. 5 is a schematic view of a porous tantalum coordinated with feeder in accordance with the present invention.

Further referring FIG. 5, the guide pin 5 is available to remove from the through hole 3 of the implantation when the porous tantalum rod is on half of implantation as shown in FIG. 4. Mashed osseous tissues can be injected into the femoral head through a feeder 6 from the through hole, thus causes the cavity of the femoral head without lesion osseous tissues filled more denser and more conducive to fix the implantation and grow of osseous tissues.

EXAMPLE 2

A method for preparing the porous tantalum material of the porous tantalum rod is provided.

The solution is a 2-8 wt % polyvinyl alcohol solution made by polyvinyl alcohol and distilled water was mixed with tantalum powder having less than 50 μm of diameter and less than 0.1% of the oxygen content to form tantalum slurry. The tantalum slurry was casted into the polyurethane foam having 0.48-0.89 mm of pore diameter, 0.015-0.065 g/cm$^3$ of density and larger than 40° of hardness until the organic foam body is filled with the tantalum slurry. The polyurethane foam body with the tantalum slurry was dried to remove water therein, degreased under inert gas to remove polyvinyl alcohol and polyurethane foam, and vacuum sintered to form a porous sintered body. The foam skeleton formed by the sintered tantalum power has tantalum particles with 50%-90% of sintered neck structures, then, vacuum annealed and treated with normal post-treatments to obtain a porous tantalum.

EXAMPLE 3

A method for preparing the porous tantalum material of the porous tantalum rod is provided.

12.5 g of polyvinyl alcohol was put in a container filled in 240 mL of water, and then the container was put on a hotplate. The polyvinyl alcohol and water are heated and agitated to form a polyvinyl alcohol solution. 60 g of tantalum powder with less than 50 μm of diameter and less than 0.1% of oxygen content was scaled by a 300 g balance an added to 50 mL of the polyvinyl alcohol solution (the polyvinyl alcohol solution was cooled). The tantalum powder and the polyvinyl alcohol solution were mix and agitated homogeneously to form tantalum slurry. The tantalum slurry was casted into a 10×10×30 mm porous polyurethane foam body (0.48 mm of pore diameter, 0.025 g/cm$^3$ of density and 50° of hardness) until the pores of the polyurethane foam body were filled with the tantalum slurry. Then, the polyurethane foam body filled with the tantalum slurry was put into a porcelain dish placed in a vacuum drier. The polyurethane foam body filled with the tantalum slurry was dried in the vacuum drier at 60° C. for 8 hours under 1Pa of vacuity. The dried polyurethane foam body filled with the tantalum slurry was degreased at 600° C. for 120 minutes under lower than 10$^{-4}$ Pa of vacuity. The dried polyurethane foam and the dried tantalum slurry were separated after the process of degreasing. Then, the dried tantalum slurry are sintered in a vacuum sintering furnace at 2200° C. for 2 hours under 10$^{-4}$ Pa of vacuity to form a porous sintered body. The argon is employed as a protective gas during sintering. The porous sintered body was cleaned out of the dust and dirt and then treated with normal post-treatments to obtain a porous tantalum.

Produced a rod with the porous tantalum material, and the rod comprises a screw thread formed on one end of rod used for connecting with osseous tissues; a ball head shaped structure formed on the other end of the rod; a slotted formed on the end-face of the screw thread providing the surgical tools ease to install and use; a through hole formed on the center of the rod.

Figure 6:
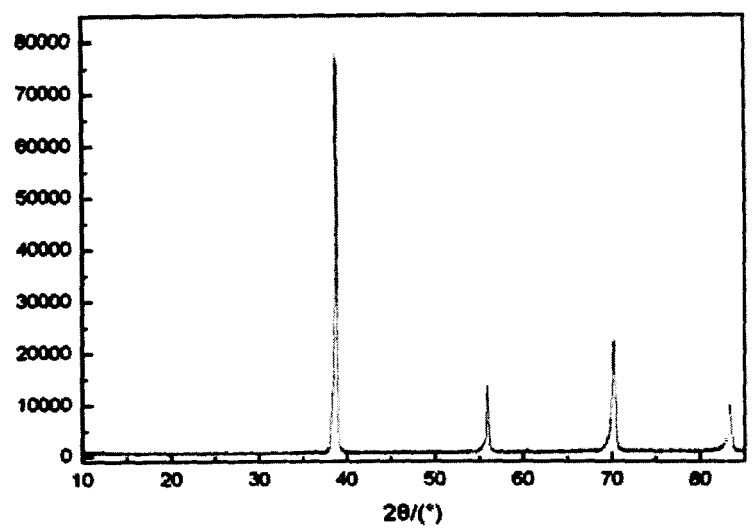
FIG. 6 is a x-ray diffraction (XRD) pattern of a porous tantalum material used for a porous tantalum rod in accordance with the present invention.
Figure 7:
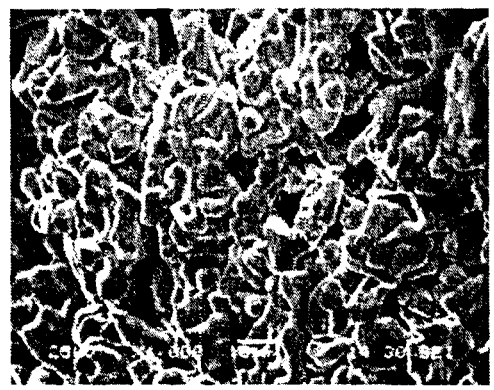
FIG. 7 is a scanning electron microscopic (SEM) macrograph of a porous tantalum material used for a porous tantalum rod in accordance with the present invention.
Figure 8:
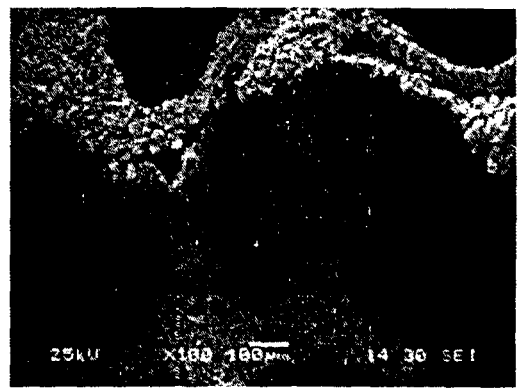
FIG. 8 is a scanning electron microscopic (SEM) micrograph of a porous tantalum material used for a porous tantalum rod in accordance with the present invention.

With reference to FIGS. 6 to 8, it is shown that the porous tantalum material made in Example 3 has a foam structure with three-dimensional interconnecting pores. The foam structure has a foam skeleton accumulated by the tantalum powder, and tantalum particles located in the foam skeleton, and sintered neck structures formed between 50% to 95% of the tantalum particles.

The density, porosity, pore diameter and other mechanical properties of the obtained porous tantalum were tested by standard test methods such as GB/T5163-2006, GB/T5249-1985, GB/T6886-2001 and the like. The porous tantalum has three-dimensional interconnecting pores and less than 0.5% of impurities. The interconnecting pores are well-distributed. The tested porous tantalum has 3.5 g/cm$^3$ of density, higher than 40% of porosity, 150 μm of average pore diameter, 2.0 GPa of elastic modulus, 35 MPa of yield strength, 40 MPa of compressive strength, 17.3% of the amount of plastic deformation, 65 MPa of tensile strength and 14.7% of percentage elongation. According to the anti-bending test on a basis of metal bending strength, the microstructure of the porous tantalum has less than 45% of fracture rate of the sintered neck structure, and larger than 55% of fracture rate of the interior of the tantalum particles.

EXAMPLE 4

A porous tantalum rod is provided, which comprises a fastening structure 1 with screw thread formed on one end of the porous tantalum rod; a ball head shaped structure 4 formed on the other end of the porous tantalum rod; a slotted 2 formed on the end-face of the fastening structure 1 providing the surgical tools ease to install and use; as shown in FIG. 3, a through hole 3 formed on the center of the porous tantalum rod.

The porous tantalum material of the porous tantalum rod has a foam structure with three-dimensional interconnecting pores, which is produced by foam impregnation. The foam structure has a foam skeleton, and tantalum particles accumulated on the foam skeleton, and multiple sintering neck structures formed between the tantalum particles.

Tantalum powder having less than 50 μm of diameter and less than 0.1% of the oxygen content as a raw material was mixed with a polyvinyl alcohol solution as a binder solution to form tantalum slurry. The tantalum slurry was casted into a polyurethane foam body. The polyurethane foam body with the tantalum slurry was dried, degreased, vacuum sintered, vacuum annealed and treated with normal post-treatments to obtain a porous tantalum.

In the exemplary embodiment, the poly urethane foam body has 0.56-0.72 mm of pore diameter, 0.025 g/cm$^3$ of density and 50°-80° of hardness;

The polyurethane foam body with the tantalum slurry was dried under 10$^{-2}$-1 Pa of vacuity to remove water. The dried polyurethane foam body and polyvinyl alcohol are separated from the dried tantalum slurry at 400-800° C. of the temperature under 10$^{-4}$-10$^{-3}$ Pa of vacuity or in a protective environment of inert gas with keeping the temperature for 30-120 minutes. The dried tantalum slurry was sintered at 2000-2200° C. under 10$^{-4}$-10$^{-3}$ Pa of vacuity and keeping the temperature for 1-5 hours. The argon or other alternative inert gas was employed as a protective gas when keeping the temperature during sintering process, to obtain a porous sintered body. After sintered, the porous sintered body was annealed by keeping the temperature at 1000-1250° C. for 1-4 hours under 10$^{-4}$-10$^{-3}$ Pa of vacuity, and then treated with normal post-treatments to obtain a porous tantalum.

EXAMPLE 5

Tantalum powder having less than 50 μm of diameter and less than 0.1% of the oxygen content as a raw material was mixed with a polyvinyl alcohol solution as a binder solution to form tantalum slurry. The tantalum slurry was casted into a polyurethane foam body having 0.48-0.89 mm of pore diameter, 0.015-0.035 g/cm³ and 50°-80° of hardness. The polyurethane foam body with the tantalum slurry was dried, degreased, vacuum sintered, vacuum annealed and treated with normal post-treatments to obtain a porous tantalum.

In the exemplary embodiment, polyvinyl alcohol was dissolved in the distilled water under heat to form a 5 wt % polyvinyl alcohol solution. 7 weight parts of tantalum powder and 1 weight part of the 5 wt % polyvinyl alcohol solution were mixed homogeneously and agitated to form pasty tantalum slurry. The polyurethane foam body was impregnated repeatedly until the pores of the polyurethane foam body were filled with the tantalum slurry;

the polyurethane foam body with the tantalum slurry was dried at 60-100° C. for 4-8 hours under 1 Pa of vacuity to remove water;

the dried polyurethane foam body were put into a tungsten device in a non-oxidizing atmosphere furnace with increasing to 800° C. at a proper rate. The dried organic foam body was degreased under argon having at least 99.999% of purity as a protective gas. The pure argon was employed as a protective gas for 30 minutes before increasing the temperature to exclude the air in the furnace. The temperature was increased from room temperature to 400° C. at a rate of 1° C./min with argon flowing at a rate of 0.5L/min and kept for 30 minutes, and then increased from 400 to 800° C. at a rate of 0.5° C./min with argon flowing at a rate of 1 L/min and kept for 120 minutes. Then, the power was closed and the degreased sample was cooled down with the temperature in the furnace while argon flowing at a rate of 1 L/min. The argon supplier was closed until the temperature of the degreased sample was decreased to the room temperature;

the degreased sample in the tungsten device was heated in a sintering furnace and sintered by increasing the temperature to 2200° C. at a proper rate. The vacuity reached to $10^{-4}$ Pa before increasing the temperature in the sintering furnace. The temperature in the sintered furnace was increased from room temperature to 1200° C. at a rate of 10-15° C./min and kept for 30 minutes under $10^{-4}$ Pa of vacuity, and then increased to 1500° C. at a rate of 10° C./min and kept for 30 min under $10^{-4}$-$10^{-3}$Pa of vacuity, and then increased to 2200° C. at a rate of 6° C./min and kept for 120 minutes under $10^{-3}$ Pa of vacuity. After sintered, under $10^{-3}$ Pa of vacuity, the temperature was decreased to 1600° C. at a rate of 10-15° C./min and kept for 30 minutes, and then decreased to 1200° C. at a rate of 12° C./min and kept for 60 min, and then decreased to 800° C. at a rate of 10° C./min. Then, the sintered sample was cooled naturally;

the sintered sample was put into the corundum container in an annealing furnace under proper vacuity and annealed by increasing the temperature to 1250° C. at a proper rate. The vacuity reached to $10^{-4}$Pa before increasing the temperature in the annealing furnace. The temperature in the annealing furnace was increased from room temperature to 1250° C. at a rate of 15° C./min and kept 240 minutes under $10^{-4}$-$10^{-3}$ of vacuity, and then decreased to 1000° C. at a rate of 5° C./min and kept for 180 min under $10^{-4}$-$10^{-3}$ Pa of vacuity, and then decreased to 800° C. at a rate of 10° C./min and kept for 120 minutes under $10^{-4}$ Pa of vacuity, and then decreased to room temperature at a rate of 20° C./min under $10^{-4}$ Pa of vacuity.

At last, the annealed sample was treated with normal post-treatments and a porous tantalum.rod described in Example 1 was obtained.

What is claimed is:

1. A porous tantalum rod, implantable into a femoral head, which is made of a porous tantalum material produced by foam impregnation and ordered steps of
    (a) obtaining three materials:
        an organic binder,
        a dispersant and
        a tantalum powder, of an average diameter of less than 50 μm, and having an oxygen content of less than 0.1% in amount;
    (b) preparing a solution by mixing the organic binder with the dispersant;
        preparing a tantalum slurry by mixing the solution with the tantalum powder;
    (c) obtaining an organic foam body with multiple pores, wherein the organic foam body is a polyurethane foam body having pores having a pore diameter of 0.48-0.89 mm, 0.015-0.065 g/cm³ in density, and of greater than 40° in hardness;
    (d) (1) casting the tantalum slurry into the organic foam body; and
        (2) impregnating the organic foam body produced by step (d)(1) with the tantalum slurry until the multiple pores are filled with the tantalum slurry;
    (e) removing the dispersant by drying the organic foam body to obtain a dried organic foam body with a dried tantalum slurry;
    (f) degreasing the dried organic foam body in a protective environment of inert gas to obtain the dried tantalum separately from the organic binder and from the dried organic foam body;
    (g) vacuum sintering the dried tantalum slurry to obtain a porous sintered body, wherein the porous sintered body includes
        a foam skeleton,
        sintered tantalum particles located on the foam skeleton, and
        multiple sintering neck structures formed between the tantalum particles; and
    (h) vacuum annealing and treating the porous sintered body with normal post-treatments to obtain the porous tantalum materials which forms the porous tantalum rod, wherein the porous tantalum rod comprising:
        a fastening structure formed on one end of the porous tantalum rod; and
        a through hole formed on a center of the porous tantalum rod, through which the rod is oriented when in the femoral head, and through which other materials are injected; and
        the porous tantalum material forming the porous tantalum rod produced in the step (h) is a foam structure of three-dimensional interconnecting pores characterized by a porosity of 30-85%, a pore diameter of 150-600 μm, and sintering neck structures formed by at least 50%-95% of the tantalum particles therebetween.

2. The porous tantalum rod as claimed in claim 1, wherein the fastening structure is a screwed structure, and having a slot formed on an end-face of the screwed structure.

3. The porous tantalum rod as claimed in claim 2, wherein another end of the porous tantalum rod is ball head shaped.

* * * * *